US007354995B2

(12) United States Patent
Imamura et al.

(10) Patent No.: US 7,354,995 B2
(45) Date of Patent: Apr. 8, 2008

(54) MAGNETIC SUBSTANCE-BIOSUBSTANCE COMPLEX STRUCTURE, PEPTIDE FRAGMENT CAPABLE OF LINKING TO MAGNETIC SUBSTANCE AND GENE THEREFOR, AND PROCESS FOR PRODUCING THE COMPLEX STRUCTURE

(75) Inventors: Takeshi Imamura, Chigasaki (JP); Tetsuya Yano, Atsugi (JP); Tsuyoshi Nomoto, Tokyo (JP); Shinya Kozaki, Tokyo (JP); Tsutomu Honma, Atsugi (JP); Akiko Tsuchitani, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 111 days.

(21) Appl. No.: 10/546,404

(22) PCT Filed: Apr. 30, 2004

(86) PCT No.: PCT/JP2004/006350

§ 371 (c)(1),
(2), (4) Date: Aug. 19, 2005

(87) PCT Pub. No.: WO2004/097416

PCT Pub. Date: Nov. 11, 2004

(65) Prior Publication Data

US 2007/0054315 A1 Mar. 8, 2007

(30) Foreign Application Priority Data

May 2, 2003 (JP) ............................. 2003-127504

(51) Int. Cl.
*C07K 7/08* (2006.01)
*C07K 17/14* (2006.01)

(52) U.S. Cl. .................. 530/327; 530/811; 530/300; 536/23.1

(58) Field of Classification Search ................ 530/327, 530/811, 300; 536/23.1
See application file for complete search history.

(56) References Cited

U.S. PATENT DOCUMENTS

| 4,812,401 | A | * | 3/1989 | Tarnowski et al. ............ 435/29 |
| 5,776,360 | A | | 7/1998 | Sieber ...................... 252/62.63 |
| 6,033,878 | A | | 3/2000 | Matsunaga ................. 435/69.7 |
| 6,853,477 | B2 | | 2/2005 | Nomoto et al. ............. 359/296 |
| 6,916,861 | B2 | | 7/2005 | Nomoto et al. ............. 523/160 |
| 6,951,745 | B2 | | 10/2005 | Nomoto et al. ............. 435/118 |
| 2003/0096115 | A1 | | 5/2003 | Kozaki et al. .............. 428/404 |
| 2003/0104302 | A1 | | 6/2003 | Honma et al. ........... 430/110.2 |
| 2003/0118931 | A1 | | 6/2003 | Yano et al. ............ 430/108.22 |
| 2003/0170716 | A1 | | 9/2003 | Yano et al. ..................... 435/6 |
| 2003/0203458 | A1 | | 10/2003 | Kozaki et al. .............. 435/135 |
| 2003/0206330 | A1 | | 11/2003 | Nomoto et al. ............. 359/296 |
| 2004/0005638 | A1 | | 1/2004 | Honma et al. ............... 435/7.1 |
| 2004/0259026 | A1 | | 12/2004 | Honma et al. ........... 430/270.1 |
| 2005/0208635 | A1 | | 9/2005 | Nomoto et al. ............. 435/135 |
| 2006/0035223 | A1 | * | 2/2006 | Naik et al. ..................... 435/6 |

FOREIGN PATENT DOCUMENTS

| EP | 1149912 A2 | 10/2001 |
| EP | 1262766 A2 | 12/2002 |
| JP | 05-080052 | 3/1993 |
| JP | 05-209884 | 8/1993 |
| JP | 07-063761 | 3/1995 |
| JP | 2001-069968 | 3/2001 |
| JP | 2001-078753 | 3/2001 |
| JP | 2002-327046 | 11/2002 |
| JP | 2003-011312 | 1/2003 |
| JP | 2003-012957 | 1/2003 |
| JP | 2003-012984 | 1/2003 |
| JP | 2003-015168 | 1/2003 |
| JP | 2003-015359 | 1/2003 |
| JP | 2003-026493 | 1/2003 |
| JP | 2003-026506 | 1/2003 |
| WO | WO 01/86248 A2 | 11/2001 |
| WO | WO 03/078451 A2 | 9/2003 |

OTHER PUBLICATIONS

Patent Abstract of Japan, vol. 013, No. 255 (C-606) Jun. 1988 for JP01/060388.
Brown, S.; Engineered iron oxide-adhesion mutants of the *Escherichia coli* phage receptor; Proc. Natl. Acad. Sic. vol. 89, pp. 8651-8655, 1992.
Gebhardt, K., et al.; "Adhesive Peptides Selected by Phage Display: Characterization, Applications and Similarities with Fibrinogen"; Peptide Research, vol. 9, No. 6, pp. 269-278 (1996).
Pistor et al., "Expression of Viral Hemagglutinin on the Surface of *E. coli*," *Klin Wochenschr*, vol. 66, pp. 110-116 (1988).
Charbit et al., "Versatility of a Vector for Expressing Foreign Polypeptides at the Surface of Gram-negative Bacteria," *Gene*, vol. 70, pp. 181-189 (1988).
Hedegaard et al., "Type 1 Fimbriae of *Escherichia coli* as Carriers of Heterologous Antigenic Sequences," *Gene*, vol. 85, pp. 115-124 (1989).
Lam et al., "A New Type of Synthetic Peptide Library for Identifying Ligand-Binding Activity," *Nature*, vol. 354, pp. 82-84 (1991).
Houghten et al., "Generation and Use of Synthetic Peptide Combinatorial Libraries for Basic Research and Drug Discovery," *Nature*, vol. 354, pp. 84-86 (1991).

(Continued)

*Primary Examiner*—Rebecca E. Prouty
*Assistant Examiner*—Rosanne Kosson
(74) *Attorney, Agent, or Firm*—Fitzpatrick, Cella, Harper & Scinto

(57) ABSTRACT

A magnetic substance-biosubstance complex structure comprises a magnetic substance-containing carrier and a biosubstance immobilized on the carrier, the biosubstance being immobilized through a spacer comprising an amino acid sequence on a surface of the carrier.

2 Claims, No Drawings

OTHER PUBLICATIONS

Fuchs et al., Targeting Recombinant Antibodies to the Surface of *Excherichia coli*: Fusion to a Peptidoglycan Associated Lipoprotein, *Bio/Technology*, vol. 9, pp. 1369-1372 (1991).

Bradbury et al., "Use of Living Columns to Select Specific Phage Antibodies," *Bio/Technology*, vol. 11, pp. 1565-1569 (1993).

Francisco et al., Production and Fluorescence-Activated Cell Sorting of *Escherichia coli* Expressing a Functional Antibody Fragment on the External Surface, *Proc. Natl. Acad. Sci. USA*, vol. 90, pp. 10444-10448 (1993).

Whaley et al., "Selection of Peptides with Semiconductor Binding Specificity for Directed Nanocrystal Assembly," *Nature*, vol. 405, pp. 665-668 (2000).

* cited by examiner

MAGNETIC SUBSTANCE-BIOSUBSTANCE COMPLEX STRUCTURE, PEPTIDE FRAGMENT CAPABLE OF LINKING TO MAGNETIC SUBSTANCE AND GENE THEREFOR, AND PROCESS FOR PRODUCING THE COMPLEX STRUCTURE

CROSS REFERENCE TO RELATED APPLICATION

This application is a submission to enter the national stage under 35 U.S.C. §371 of PCT Application No. PCT/JP2004/006350.

TECHNICAL FIELD

The present invention relates to a magnetic substance-biological substance complex type structure, a peptide fragment and a gene having an amino acid sequence capable of linking to the magnetic substance for preparation of the structure, and a process for producing the magnetic substance-biological substance complex type structure. (Hereinafter the "biological substance" is referred to as a "biosubstance".) In particular the present invention relates to a structure containing a biosubstance immobilized on a magnetic substance-containing carrier which is useful in biochemical fields and medical field as carriers of diagnostic agents, carriers for separation of bacteria or biological cells, carriers for separation and purification of nucleic acids or proteins, carriers for drug delivery, carriers of enzyme reaction, carriers for cell culture, and carriers for drug screening; and to a process for producing the structure.

BACKGROUND ART

A magnetic substance-containing structure, which is readily collectable by magnetic force, is promising for use mainly in biochemical fields as carriers of diagnostic agents, carriers for separation of bacteria or biological cells, carriers for separation and purification of nucleic acids or proteins, carriers for drug delivery, carriers for enzyme reaction, carriers for cell culture, and carriers for like uses. Further, the structure is promising as a carrier in drug-screening fields for selecting efficiently a target substance having an intended physiological activity or pharmacological activity from possible drug substances containing a biopolymer such as nucleic acids, peptides, proteins, and carbohydrates.

In such applications, in utilizing the magnetic substance-containing structure as a carrier, a means is necessary for immobilizing and holding the physiologically active substance on the surface of the magnetic substance-containing structure. Methods for the immobilization are disclosed in literature as below.

Japanese Patent Application Laid-Open No. H05-209884 discloses use of magnetic particles extracted from a magnetic bacteria as a carrier for immobilizing an antibody fragment on the surface of the magnetic particles. The magnetic particles derived from a magnetic bacterium are coated with a lipid film on the surface. On this lipid film, an antibody fragment is immobilized by utilizing N-succinimidyl 3-(2-pyridylthio)propionate.

Japanese Patent Application Laid-Open No. H05-080052 discloses immobilization of anti-rabbit IgG on ferrite particles prepared by coating of polymer particles mainly composed of polystyrene with $Fe_3O_4$ as the carrier modifying the particle surface by a—$(CH_2)_3NHCO(CH_2)_3CONH(CH_2)_6NH_2$ group by use of a coupling agent.

Japanese Patent Application Laid-Open No. H07-063761 discloses a process for producing a fine particulate magnetic substance for immobilizing a physiologically active substance in which fine magnetic particles of average diameter of 0.3-1.0 μm are fixed onto resin particles of average diameter of 1.0-10 μm as the nuclei by a high-speed gas stream impact method; the fixed magnetic fine particles are surface-treated with a silane coupling agent; and a physiologically active substance is bonded thereon directly or through another functional group introduced thereto.

U.S. Pat. No. 5,776,360 discloses a method in which magnetite fine particles are surface treated for aminosilanation, and HCG (human chorionic gonadotropin) antibody is immobilized thereon with glutaraldehyde by utilizing the introduced amino group.

The aforementioned prior art techniques utilize a chemical covalent bond between the biosubstance and the magnetic substance for immobilizing a biosubstance on a magnetic substance contained in a carrier. Such a technique is liable to cause conversion or denaturation of the biosubstance depending on the covalent bond formation conditions (such as temperature, pH, and reagent). For example, the site exhibiting an inherent function of the biological material (e.g., molecular recognition site, and catalyst site) can be modified by introduction of a reagent to affect adversely the inherent function of the biosubstance. Otherwise, the covalent bond can be formed near the active site of the inherent function of the biosubstance to impair the inherent function exhibition.

As the results of the above adverse effects, the obtained biosubstance-holding carrier may not achieve the intended inherent function as the carrier of a medical diagnostic drug, the carrier for separation of bacteria or cells, the carrier for separation and purification of nucleic acids or proteins, the carrier for drug delivery, the carrier for enzyme reaction, the carrier for cell culture, or the carrier for drug screening.

The present invention provides a novel method for immobilizing a biosubstance like a protein on a carrier containing a magnetic substance, wherein the biosubstance is immobilized on the magnetic substance surface with the function kept active, and enabling immobilization of the intended biosubstance selectively onto the magnetic substance surface. The present invention provides also a magnetic substance-biosubstance complex structure, and a process for producing thereof.

DISCLOSURE OF THE INVENTION

After comprehensive investigation to solve the above problems, the inventors of the present invention found that a peptide having a specified amino acid sequence can be linked to a magnetic substance surface stably with high reproducibility, and further found that a biosubstance-spacer complex which is formed from the biosubstance and a spacer having a peptide fragment containing an amino acid sequence linkable to the aforementioned magnetic substance can be immobilized on the magnetic substance by the linking ability of the spacer portion. Furthermore, the inventors of the present invention confirmed that the biosubstance-spacer complex itself having the spacer preliminarily linked thereto can be prepared in a state so as to perform effectively the inherent function, and consequently, the biosubstance-spacer complex, when immobilized on the surface of the magnetic substance, can be held with its function kept active.

The inventors of the present invention found also that the peptide fragment having the amino acid sequence linkable to a desired magnetic substance can readily be obtained from a random peptide library in dependence upon the linking ability to the magnetic substance, and with the amino acid sequence of the peptide fragment, the spacer containing the peptide fragment having an amino acid sequence capable of linking to the Magnetic substance can be designed readily. In addition to the above findings, the inventors of the present invention found that a biosubstance-spacer complex retaining the inherent function can be prepared from various biosubstances, and the structures which are obtained by immobilizing a biosubstance through a spacer containing a peptide fragment having an amino acid capable of linking directly to the magnetic substance are useful for various applications and purposes. The present invention has been accomplished based on the above findings.

The magnetic substance-biosubstance complex structure of the present invention comprises a magnetic substance-containing carrier and a biosubstance immobilized on the carrier, the biosubstance being immobilized through a spacer comprising an amino acid sequence on a surface of the carrier. The spacer comprises preferably a peptide structure comprising two or more amino acid units.

The peptide structure comprising two or more of amino acid units is preferably a peptide fragment comprising an amino acid sequence capable of linking to the magnetic substance. The amino acid sequence capable of linking to the magnetic substance can be selected from a random peptide library in dependence upon capability of linking to the magnetic substance.

In the magnetic substance-biosubstance complex structure of the present invention, the biosubstance is preferably one or more biosubstances selected from the group consisting of nucleic acids, proteins, carbohydrates, lipids, and complexes thereof. For example, the protein is suitably a polyhydroxyalkanoate-synthesizing enzyme.

In the magnetic substance-biosubstance complex structure of the present invention, the magnetic substance comprises preferably an $MO \cdot Fe_2O_3$ structure (M: bivalent metal) or an $Fe_2O_3$ structure, and for the magnetic substance the amino acid sequence in the spacer is one or more of amino acid sequences and/or complexes selected from the group consisting of amino acid sequences represented by SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30; and complex thereof.

Correspondingly, the present invention provides also peptide fragments having an amino acid sequence capable of linking to the magnetic substance and being useful as the peptide structure contained in the spacer. The peptide fragment having an amino acid sequence capable of linking to the magnetic substance is exemplified by peptide fragments containing an amino acid sequence selected from the group consisting of SEQ ID NO:15 through SEQ ID NO: 30.

Further, the genetic DNA of the present invention for coding a peptide fragment having an amino acid sequence capable of linking to the magnetic substance is exemplified by genetic DNAs comprising a DNA coding the peptide fragments containing an amino acid sequence capable of linking to the magnetic substance selected from the group consisting of SEQ ID NO:15 through SEQ ID NO: 30.

The biosubstance-spacer complex of the present invention which is prepared by linking of a spacer containing a peptide fragment having an amino acid sequence capable of linking to the magnetic substance is exemplified by fusion type polyhydroxyalkanoate polymerization enzyme proteins which are fusion type proteins prepared by fusion of a peptide comprising an amino acid sequence selected from the group of SEQ ID NO:15 through SEQ ID NO:30 with a polyhydroxyalkanoate polymerization enzyme protein represented by SEQ ID NO:1 or SEQ ID NO:3.

The process of the present invention for producing the a structure having a biosubstance immobilized on a magnetic substance-containing carrier through a spacer comprising an amino acid sequence comprises
(1) a step of preparing a biosubstance-spacer complex formed by linking the spacer and the biosubstance, and
(2) a step of bringing the biosubstance-spacer complex with the carrier;

wherein the biosubstance is immobilized by linking a portion of the spacer of the biosubstance-spacer complex to the surface of the carrier. In the process, the spacer comprises preferably a peptide structure comprising two or more amino acid units.

In utilizing the spacer having a peptide structure constituted of two or more amino acid units, the biosubstance contains a protein, the step of producing a biosubstance-spacer complex includes an operation of expressing a fusion type protein constituted of the peptide structure and the protein joined together according to joined gene having a base sequence formed by joining a base sequence coding amino acid sequence of the protein and a base sequence of coding the amino acid sequence of the peptide structure; and the biosubstance-spacer complex can be prepared by the fusion type protein. For instance, the above constitution can be employed suitably, when the protein included in the biosubstance is a polyhydroxyalkanoate-synthesizing enzyme.

The process for producing the magnetic substance-biosubstance complex structure of the present invention is useful when the magnetic substance comprises an $MO \cdot Fe_2O_3$ structure (M: bivalent metal) or an $Fe_2O_3$ structure. With such a magnetic substance, the amino acid sequence in the spacer is one or more of amino acid sequence and/or complexes selected from the group consisting of amino acid sequences represented by SEQ ID NO:15 through SEQ ID NO:30.

The term "a magnetic substance-biosubstance complex structure" as the object of the present invention means a structure which is constituted of a carrier containing a magnetic substance, and a biosubstance in a form of a complex immobilized in a state of an immobilized layer on the surface of the carrier.

BEST MODE FOR CARRYING OUT THE INVENTION

Being different from conventional chemical method of fixing chemically a biosubstance onto a magnetic substance surface through a covalent bond, the magnetic substance-biosubstance complex structure of the present invention is prepared, for example, through the steps below: a peptide fragment capable of linking to a desired magnetic substance is obtained simply by screening of random peptide library for the capability of linking to the magnetic substance; a spacer is designed which contains the peptide fragment having an amino acid sequence capable of linking to the magnetic substance corresponding to the amino acid sequence; a biosubstance-spacer complex is prepared by linking the spacer with the biological material; and the resulting biosubstance-spacer complex is immobilized on the surface of the magnetic substance surface.

Therefore, in this method, the biosubstance-spacer complex can be confirmed preliminarily to have the inherent function of the biosubstance. Therefore, in subsequent operation of immobilization of the biosubstance-spacer complex on the magnetic substance surface, the biosubstance immobilized on the magnetic substance surface is kept in a state to exhibit the inherent function when biosubstance is immobilized on the magnetic substance surface, since no chemical reaction with a reagent or the like affecting the function of the biosubstance is employed. Further, the amino acid sequence having linking capability can be selected by screening corresponding to the employed magnetic substance, and the linking state of the spacer to be linked preliminarily to the biosubstance and the amino acid sequence capable of linking to the magnetic substance contained in the spacer can be designed. Therefore, the magnetic substance-biosubstance complex structure can employ in wide ranges of the used magnetic substance and the objective biosubstance.

The present invention is described below in more detail.

<Magnetic Substance>

The "magnetic substance" for constituting the magnet-containing carrier in the present invention may be suitably selected without limitation, provided that the peptide having an amino acid sequence of the spacer is capable of linking with the carrier by its affinity. The kind and structure of the magnetic substance may be suitably selected in correspondence with the conditions of immobilization of the biosubstance through the linking spacer and with the application conditions of the produced magnetic substance-biosubstance complex structure. The magnetic substance-containing carrier of the present invention includes structures in shapes of granules, fibers, needles, flat plates, and films containing a magnetic substance as the constituent therein.

The magnetic substance for constituting the carrier of the present invention includes metals and metal compounds having magnetism: specifically ferrites such as iron tritetraoxide ($Fe_3O_4$), γ-sesquioxide ($γ-Fe_2O_3$), MnZn-ferrite, NiZn-ferrite, YFe-garnet, GaFe-garnet, Ba-ferrite, and Sr-ferrite; metals such as iron, manganese, cobalt, nickel, and chromium; alloys of iron, manganese, cobalt, nickel, and the like, but not limited thereto. For instance, for deposition and immobilization of a biosubstance complex, or for administration of the structure formed by depositing and immobilizing a biological complex to a living body, various ferrite compositions are useful which are prepared by substituting at least a part of the metal element of magnetite by other metal element in place of magnetite ($Fe_3O_4$) well adaptable to living bodies. The shape of the magnetic substance varies depending on the formation conditions, taking a shape such as a polyhedron, octahedron, hexahedron, sphere, bar, and scale. A less anisotropic structure of the magnetic substance is preferred as the carrier for the stable performance of the function. The primary particle size of the magnetic substance constituting the magnet-containing carrier of the present invention may be selected depending on the usage thereof, and may be, for instance, in the range from 0.001-10 μm.

The magnetic substance constituting the magnet-containing carrier of the present invention may be super-paramagnetic. For instance, ferrite particles having a small particle size of not more than 20 nm become superparamagnetic owing to thermal disturbance effect and lose residual magnetization and coercivity. Even if the particles are superparamagnetic, the particles can be operated magnetically by application of external magnetic field. Further, the superparmagnetic particles, which have no residual magnetization or coercivity, will not aggregate together magnetically when external magnetic field is not applied.

The magnet-containing carrier employed in the present invention may contain a simple magnetic substance or a composite of two or more of the magnetic substances.

The magnet-containing carrier may contain the aforementioned magnetic substance on a usual polymer compound or an inorganic solid such as a resin, glass, ceramic, a metal, and a metal oxide by mixing, vapor deposition, plating or the like method. However, for immobilizing the biosubstance on the magnet-containing material, the magnetic substance should be bared at least on a part of the surface of the magnetic substance.

Examples of the constituting material of magnet-containing carrier other than the magnetic substance includes organic polymers produced by polymerization of a polymerizable monomer: the monomer including styrenic polymerizable monomers such as styrene, α-methylstyrene, β-methylstyrene, o-methylstyrene, m-methylstyrene, p-methylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, and p-phenylstyrene; acrylic polymerizable monomers such as methyl acrylate, ethyl acrylate, n-propyl acrylate, isopropyl acrylate, n-butyl acrylate, isobutyl acrylate, t-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethylphosphatoethyl acrylate, diethylphosphatoethyl acrylate, dibutylphosphatoethyl acrylate, and 2-benzoyloxyethyl acrylate; methacrylic polymerizable monomer such as methyl methacrylate, ethyl methacrylate, n-propyl methacrylate, isopropyl methacrylate, n-butyl methacrylate, isobutyl methacrylate, t-butyl methacrylate, n-amyl methacrylate, n-hexyl methacrylate, 2-ethylhexyl methacrylate, n-octyl methacrylate, n-nonyl methacrylate, diethylphosphatoethyl methacrylate, and dibutylphosphatoethyl methacrylate; methylene-aliphatic monocarboxylic acid esters; vinyl polymerizable monomer such as vinyl esters such as vinyl acetate, vinyl propionate, vinyl benzoate, vinyl butyrate, vinyl benzoate, and vinyl formate; vinyl ethers such as vinyl methyl ether, vinyl ethyl ether, and vinyl isobutyl ether; and vinyl ketones such as vinyl methyl ketone, vinyl hexyl ketone, and vinyl isopropyl ketone.

Other examples of the constituting material of magnet-containing carrier other than the magnetic substance are inorganic solids, including clay minerals such as kaolinite, bentonite, talc, and mica; metal oxides such as alumina, titanium dioxide, and zinc oxide; insoluble inorganic salts such as silica gel, hydroxyapatite, and calcium phosphate gel; metals such as gold, silver, platinum, and copper; and semiconductor compounds such as GaAs, GaP, and ZnS. The material is not limited thereto.

The material other than the magnetic substance may be used in combination of two or more thereof.

The shape of the carrier formed by use of the constituting material in addition to the magnetic substance is preferably particulate generally in consideration of application of the produced magnetic substance-biosubstance complex structure. However, in some application fields, the carrier may be in a shape of a film of a plastic material such as polyethylene terephthalate (PET), diacetate, triacetate, cellophane, celluloid, polycarbonate, polyimide, polyvinyl chloride, polyvinylidene chloride, polyacrylates, polyethylene, polypropylene, and polyesters; a porous film of a polymer such as polyvinyl chloride, polyvinyl alcohol, acetylcellulose, polycarbonate, nylon, polypropylene, polyethylene, and Teflon; a wood plate; a glass plate; a silicon substrate; a cloth formed from a material such as cotton, rayon, acrylic fiber, silk, and polyester fiber; and a paper sheet such as wood free paper, medium-quality paper, art paper, bond paper, regenerated paper, baryta paper, cast-coated paper, corrugated board paper, and resin-coated paper. Naturally the shape of the carrier is not limited thereto. The material in a shape of a film or sheet may have a smooth surface or a rough surface insofar as the magnetic substance can be held thereon.

<Biosubstance>

The term "biosubstance", which is to be immobilized on the carrier containing the magnet in the magnetic substance-biosubstance complex structure of the present invention includes nucleic acids, proteins, carbohydrates, lipids, and complexes thereof, specifically including a biomolelcule selected from the group consisting of nucleic acid, protein, carbohydrate, and lipid, more specifically including at least one selected from the group consisting of DNA, RNA, aptamer, gene, chromosome, cell membrane, viruse, antigen, antibody, lectin, hapten, hormone, receptor, enzyme and peptide. Any material containing the above biosubstance can be employed in the present invention. Further, the bacteria or cells thereof producing the above "biosubstance" can be employed as the objective biological material in the present invention. In the production of the magnetic substance-biosubstance complex structure by use of the spacer containing an amino acid sequence for linking to the magnetic substance, especially in a state of fusion-body with the peptide structure, by immobilization on the carrier containing the magnetic substance as described later, the biosubstance contains preferably a peptide chain capable of fusion with the peptide structure, in particular a protein.

<Amino Acid Sequence-Containing Peptide Structure Capable of Linking to Magnetic Substance>

The amino acid sequence capable of linking to the magnetic substance in the present invention is the one selected by screening of a random peptide library, or designed reasonably in consideration of the chemical properties of the magnetic substance.

The random peptide library utilizable in screening for selection of the amino acid sequence capable of linking with the magnetic substance in the present invention includes a random synthetic peptide libraries obtained by chemical synthesis of random peptide in a soluble form; solid-phase immobilized peptide libraries synthesized on resin beads; peptide libraries biosynthesized in a ribosome cell-free system containing a chemically synthesized random DNA sequence, such as a phage display peptide library prepared by linking a random synthetic gene with an E-end side gene of surface protein of M13 type phage (e.g., gene III protein); and random peptide libraries obtained in a similar method by fusion of bacterial membrane protein, Omp A (Francisco et al.: 1993, PNAS, 90, 10444-10448, or Pistor and Hoborn, 1989, Klin.Wochenschr., 66, 110-116), PAL (Fuchs et al.: 1991, Bio/Technology, 9, 1369-1372), Lamb (Charbit et al.: 1988, Gene, 70, 181-189, and Bradbury et al.: 1993, Bio/Technology, 1565-1568), Fimbrin (Hedegaard and Klemm: 1989, Gene, 85, 115-124, and Hofnung: 1991, Methods Cell Biol., 34, 77-105), or a β-region of IgA protease (Klauser et al.: 1990, EMBO J., 9, 1991-1999).

Typical examples of the method of screening the amino acid sequences capable of linking to the magnetic substance employ chemically synthesized peptide library, or phage display peptide libraries.

When a chemically synthesized peptide library is utilized, the peptide library is brought into contact with the magnetic substance, the peptide not linkable to the magnetic substance is removed, then the peptide having been linked to the magnetic substance is recovered, and the amino acid sequence thereof is determined by an Edman degradation method or a like methods Otherwise, when a phage display peptide library is utilized, the library is brought into contact with the surface of a particulate magnetic substance immobilized on a column or a plate or with the surface of a plate-shaped magnetic substance, non-linked phage is washed off, thereafter the remaining linked phage is eluted with an acid or the like, the eluted phage solution is neutralized, and the phage is allowed to infect *Escherichia coli* to amplify the phage. By repeating this selection operation several times, plural clones capable of linking to the objective magnetic substance are concentrated. Then to obtain single clone, the *Escherichia coli* is infected with the clones and is allowed to form colonies on a culture plate. The respective single colonies are cultivated in a liquid culture medium. The phage in the supernatant of the culture is precipitated and purified by use of polyethylene glycol or the like. Analysis of the base sequence of the random region of the monoclone phage gives the peptide structure capable of linking with the magnetic substance.

The selective screening of the peptide capable of linking to the magnetic substance by use of a phage display peptide library includes an operation of concentration of the phage capable of linking stronger to the magnetic substance, a so-called panning operation. Therefore, this method enables selection of a promising peptide with higher reliability, and is applicable suitably in the present invention. The display random peptide library can be constructed, for example, by connecting a random synthesized gene with an N-end side gene of the surface protein of M13 type phage (e.g., gene III protein). The construction examples are disclosed by Scott, J K. and Smith, G P: Science, vol. 249, 386, 1990; and Cwirla, S E et al.: Proc. Natl. Acad. Sci. USA, vol. 87, 6378, 1990, and so forth. The size of the random synthesized gene is not limited, provided that the peptide can be stably expressed. In order that the prepared random peptide library includes all random sequence and has capability of linking to the magnetic substance, the size corresponds preferably to 6-40 amino acids (corresponding to the molecular weight of about 600-4000), more preferably 7-18 amino acids. The phage capable of linking to an objective magnetic substance is selected in the following procedure. The magnetic substance is fixed on a column or plate, the above library is brought into contact with the magnetic substance, non-linked phage is washed off, thereafter the remaining linked phage is eluted with an acid or the like, the eluted phage solution is neutralized with a buffer solution, and the phage is allowed to infect *Escherichia coli* to amplify the phage. By repeating the selection operation several times, plural clones capable of linking to the objective magnetic substance are concentrated. Then to obtain a monoclone, the clones are allowed to infect the *Escherichia coli* and are allowed to form colonies on a culture plate. The respective single colonies are cultivated in a liquid culture medium. The phage in the supernatant of the culture is precipitated and purified by use of polyethylene glycol or the like. Analysis of the base sequence of the random region of the monoclone phage gives the peptide structure (amino acid sequence) capable of linking to the magnetic substance.

The peptide library having a random amino acid sequence can also be prepared by use of a chemically synthesized peptide, similarly as in the above-mentioned method employing a phage. The process of preparation of a chemically synthesized peptide library includes a process employing beads (Lam, K S et al.: Nature, 354, 82, 1991), a liquid-phase focusing process (Houghton, R A et al.: Nature, 354, 84, 1991), a microplate process (Fodor, S P A et al.: Science, 251, 767, 1991), and so forth. Any of these processes is useful for the screening in the present invention.

In the case where two or more kinds of peptides capable of linking to the magnetic substance have been obtained, at least one selected from the peptides, or a peptide having an amino acid sequence prepared by combining all or a part of the amino acid sequences of the peptides in series may be used as the peptide capable of linking to a magnetic substance. In combining two of the amino acid sequences, a suitable linker sequence is preferably inserted between the combined two amino acid sequences. The linker sequence is preferably contains about 3 to about 400 amino acid units. More preferably, the linker sequence will not suppress the function of the biosubstance (e.g., a PHA synthase) in the formed complex, and will not prevent the linking reaction of the objective biosubstance complex with the magnetic substance with any of the linked two amino acid sequences. The amino acid sequence capable of linking to the magnetic substance utilized in the present invention may be an amino acid sequence reasonably designed in consideration of the chemical properties of the magnetic substance as well as the one decided by screening of a random peptide library.

<Deposition and Immobilization of Biosubstance>

The biosubstance is immobilized on a magnetic substance through a spacer having a peptide structure. The spacer forms a complex with the biosubstance and contains an amino acid sequence capable of linking to the magnetic substance in the present invention.

Specifically, for deposition and immobilization of the biosubstance on the magnetic substance, a biosubstance-spacer complex is firstly prepared by linking the biosubstance with a spacer having a peptide structure containing an amino acid sequence capable of linking with the magnetic substance, and then the resulting biosubstance-spacer complex is brought into contact with the magnetic substance in an aqueous medium to form a linkage of the magnet with the peptide structure containing the amino acid sequence capable of linking with the magnet.

The aqueous medium used in the deposition-immobilization process should be selected not to cause retardation of the immobilization reaction between the magnetic substance and the peptide structure containing the amino acid sequence capable of linking with the magnetic substance, and further to allow the deposited and immobilized biosubstance to perform its function.

The aqueous medium to allow the biosubstance to perform its function includes buffer solutions. The buffer solutions include ordinary buffer solutions useful in biochemical reactions such as acetate buffers, phosphate buffers, calcium phosphate buffers, 3-(N-morpholino)propanesulfonate (MOPS) buffers, N-tris(hydroxymethyl)-methyl-3-amino-propanesulfonate (TAPS) buffers, tris hydrochloric acid buffers, glycine buffers, and 2-(cyclohexylamino)-ethane-sulfonate (CHES) buffers. The concentration of the buffer solution for performance of the function of the biosubstance is in a usual range from 5 mM to 1.0 M, preferably from 10 to 200 mM. The pH of the solution is in the range from 5.5 to 9.0, preferably from 7.0 to 8.5, but may be outside the above range depending on the optimum pH or pH-stability of the applied biosubstance.

In the case where the magnetic substance is powdery, a suitable kind of surfactant may be added thereto to keep the powdery magnetic substance in a dispersion state in the aqueous medium in the deposition, immobilization, and later steps within the concentration range not to impair the function of the biosubstance. The surfactant includes anionic surfactants such as sodium oleate, sodium dodecylsulfonate, sodium dodecylsulfate, sodium dodecyl-N-sarcosinate, sodium cholate, sodium deoxycholate, and sodium taurodeoxycholate; cationic surfactants such as cetyltrimethylammonium bromide, and dodecylpyridinium chloride; amphoteric surfactants such as 3-[(cholamidopropyl)dimethylammonio]-1-propanesulfonic acid (CHAPS), 3-[(3-cholamidopropyl)dimethylammonio]-2-hydorxy-1-propanesulfonic acid (CHAPSO), palmitoyllysolecithin, and dodecyl-β-alanine; and nonionic surfactants such as octylglucoside, octylthioglucoside, heptylthioglucoside, decanoyl-N-methylglucamide (MEGA-10), polyoxyethylene dodecyl ether (Brij, Lubrol), polyoxyethylene-isooctylphenyl ether (Triton X), polyoxyethylene nonyl phenyl ether (Nonidet P-40, Triton N), polyoxyethylene fatty acid ester (Span), and polyoxyethylene sorbitol ester (Tween).

For keeping the dispersion state of the powdery magnetic substance in the aqueous medium, a suitable kind of auxiliary solvent may be added within a concentration range not to retard the deposition-immobilization step, and subsequent steps, and not to impair the function of the biosubstance. The auxiliary solvent may be one or more of the solvent selected from the group of linear aliphatic hydrocarbons such as hexane; monohydric alcohols such as methanol and ethanol; polyhydric alcohols such as glycerol; and derivatives of fatty acid ethers and carboxylic acid esters.

The composition of the aqueous medium for mixing the magnetic substance and the biosubstance complex is decided preferably in consideration of the fact that, in the deposition-immobilization steps, the magnetic substance and the biosubstance complex, especially the peptide structure containing the amino acid sequence capable of linking with the magnetic substance contained in the spacer portion, vary their charge polarity, charge quantity, and hydrophobicity depending on the pH and salt concentration of the aqueous medium. For example, in the case where the linking force depends on the ion adsorption between the magnetic substance and the peptide structure containing the amino acid sequence capable of linking with the magnetic substance, the electric charge contributing the adsorption of the peptide structure on the magnetic substance can be increased by lowering the salt concentration, and the opposing charge can be increased by changing the pH. On the other hand, in the case where the linking between the magnetic substance and the peptide structure is caused mainly by hydrophobic adsorption, the hydrophobicity of the both can be increased by increasing the salt concentration. The composition suitable for the adsorption can be decided by investigating the charging state and the hydrophobicity of the magnetic substance and the peptide structure by measurement by the electrophoresis and the wetting angle.

<Biosubstance-Peptide Fusion Product>

The amino acid sequence of the peptide capable of linking with the magnetic substance obtained by the aforementioned method may be fused with a desired protein for preparation of the biosubstance complex according to a conventional genetic engineering technique, when the biosubstance is a protein. For instance, the polypeptide capable of linking with the magnetic substance may be linked to an amino end (—NH$_2$) or a carboxyl end (—COOH) of the aforementioned protein to express fusion protein by gene recombination. In this fusion protein, in the linking portion between the peptide portion capable of linking to the magnetic substance and the objective protein, one or more, units of amino acids may be inserted as a linker sequence. The linker sequence contains preferably about 3 to about 400 amino acid units. The linker sequence may contain any amino acid. More preferably, the linker sequence will not suppress the function of the protein, and will not prevent the linking with the magnetic substance by employing the peptide capable of linking with the magnetic substance. Therefore, a protein-peptide fusion type biosubstance complex can be obtained in which a spacer containing the amino acid sequence of the peptide capable of linking the magnetic substance and containing another amino acid sequence having the aforementioned linker sequence as necessary.

In the magnetic substance-biosubstance complex structure of the present invention, the protein as the biosubstance may be any protein which can be immobilized according the above method. When a fusion protein is prepared by fusion with the aforementioned peptide, the gene sequence is preferably to be known, whereas when the linking with the peptide capable of linking with the magnetic substance is conducted chemically, the gene sequence need not be known.

When the biosubstance is a protein having a known gene sequence, the biosubstance-peptide structure fusion product can be directly recombined and recovered as a fusion protein constituted of the peptide structure and the protein, for example by using a host bacterium strain like *Escherichia coli*.

In the case where the biosubstance is a protein having an unknown gene sequence, a nucleic acid, or a carbohydrate, a complex can be prepared by linking after the biosubstance and/or the spacer containing the peptide structure is chemically modified or transformed without impairing the function. Specifically, one or both of the biosubstance and the spacer containing the peptide structure is modified or transformed into any of the combinations of groups of maleimido and sulfanyl (—SH), succinimido and amino, isocyanato and amino, halogeno and hydroxyl, halogeno and sulfanyl (—SH), epoxy and amino, and epoxy and sulfanyl (—SH), and then a chemical bonding is formed between the above functional groups.

In the case where the biosubstance is a lipid, a spacer complex of a lipid-spacer containing a peptide structure can be obtained by preparing a "spacer" by linking a "hydrophobic peptide structure" containing plural amino acids having a free hydrophobic group such as alanine, valine, leucine, isoleucine methionine, tryptophan, phenylalanine, and proline to the magnet-linking peptide structure, and bonding the hydrophobic peptide structure to the lipid by hydrophobic bonding.

<Polyhydroxyalkanoate-Synthesizing Enzyme>

In the magnetic substance-biosubstance complex structure of the present invention, an example of the protein employed as the biosubstance immobilized on the magnetic substance is a polyhydroxyalkanoate-synthesizing enzyme (hereinafter referred to as a "PHA synthase").

The polyhydroxyalkanoate (hereinafter referred to as "PHA") is an aliphatic polyester synthesized by PHA synthase of a microorganism, and is a promising material for use for application in biochemistry and medical treatment because the PHA is biodegradable and biocompatible, and various functional groups can be introduced to the side chains thereof. In recent years, complex materials have come to be developed which have a PHA coating on a surface of a core structure (Japanese Patent Application Laid-Open Nos. 2002-327046, 2003-11312, etc.). Such complex materials are useful in various application fields since the complex have both the functions of the core structure and the properties of the PHA coating combinedly (Japanese Patent Application Laid-Open Nos. 2003-12957, 2003-15168, 2003-12984, 2003-15359, 2003-26506, and 2003-26493).

One embodiment of the magnetic-biosubstance complex structure is a magnet-PHA synthase complex type structure which contains a PHA synthase immobilized on a magnetic substance-containing carrier. In copresence of this structure with a PHA monomer unit precursor, a magnetic complex material can be produced which is constituted of the magnet-PHA synthase complex structure coated with PHA synthesized by the PHA synthase. The magnetic composite material coated with PHA is promising in various industrial fields including biochemical and medical fields.

The PHA synthase itself as the biosubstance to be immobilized on a magnetic substance may be the one produced by a microorganism selected suitably from microorganisms capable of producing the PHA synthase, or by a transformant having a PHA synthase gene of microorganism introduced by a transformant.

The microorganisms which produce the PHA synthase include *Aeromonas* sp., *Alcaligenes* sp., *Chromatium* sp., *Comamonas* sp., *Methylobacterium* sp., *Paracocuus* sp., and *Pseudomonas* sp., and further include the microorganism isolated by the inventor of the present invention such as *Burkholderia cepacia* KK01, *Ralstonia eutropha* TB64, and *Alcaligenes* sp. TL2. Of these microorganisms, KK01 strain, TB64 strain, and TL2 strain are deposited with deposit numbers respectively of FERM BP-4235, FERM BP-6933, and FERM BP-6913 and deposited date of respectively Mar. 11, 1992, Nov. 9, 1999 and Oct. 12, 1999, to International Patent Organism Depositary in National Institute of Advanced Industrial Science and Technology (independent administrative cooperation), AIST Tsukuba Central 6, 1-1, Higashi 1-chome, Tsukuba-shi, Ibaraki-ken 305-8566 Japan, which is the international depositary authority according to "Budapest Treaty on the International Recognition of the Deposit of Microorganisms for the Purpose of Patent Procedure".

Further, PHA synthases are useful which are derived from a *Pseudomonas* microorganism such as *Pseudomonas oleoborans, Pseudomonas resinoborans, Pseudomonas* sp. 61-3, *Pseudomonas putida* KT2442, and *Pseudomonas aeruginosa*; the microorganisms isolated by the inventors of the present invention such as *Pseudomonas putida* P91, *Pseudomonas cichorii* H45, *Pseudomonas cichorii* YN2, and *Pseudomonas jessenii* P161; and *Burkholderia* bacteria such as *Burkholderia* sp. OK3, FERM P-17370 disclosed in Japanese Patent Laid-Open No. 2001-78753, and *Burkholderia* sp. OK4, FERM P-17371 disclosed in Japanese Patent Application Laid-Open No. 2001-69968. Further, PHA synthases are useful which are derived from the microorganisms such as *Aeromonas* sp. and *Comamonas* sp. producing mcl-PHA or unusual-PHA.

P91 strain (Deposit No. FERM BP-7373), H45 strain (Deposit No. FERM BP-7374), YN2 strain (Deposit No. FERM BP-7375), and P161 strain (Deposit No. FERM BP-7376), these four types of strains are deposited on Nov. 20, 2002 at International Patent Organism Depositary in National Institute of Advanced Industrial Science and Technology (independent administrative cooperation), AIST Tsukuba Central 6, 1-1, Higashi 1-Chome, Tsukuba-shi, Ibaraki-ken 305-8566 Japan, which is the international depositary authority according to "Budapest Treaty on the International Recognition of the Deposit of Microorganisms for the Purpose of Patent Procedure". The bacteria which are deposited domestically to International Patent Organism Depositary in National Institute of Advanced Industrial Science and Technology are tagged respectively with the deposit numbers.

The intended PHA synthase can be produced by recombination by use of a transformant having PHA synthase gene derived from the aforementioned PHA-producing bacterium. Conventional methods can be employed for the cloning of the PHA synthase gene derived from a PHA-producing bacterium, construction of an expression vector for recombination production, and preparation of a transformant employing the expression vector.

The isolation and purification of the PHA synthase can be conducted by any method, insofar as the enzymatic activity of the PHA synthase is retained. For example, a mass of a PHA synthase-producing microorganism is crushed by a French press or a supersonic crusher or with lysozyme or a surfactant, the crude enzyme solution obtained by centrifugation or a deposit derived form the crude enzyme solution by salting out with ammonium sulfate is purified by a purification means such as affinity chromatography, cation or anion exchange chromatography, gel filtration, or combination thereof to obtain purified enzyme protein. The gene recombinant protein can be purified more simply by binding a "tag" like a histidine residue to express a fusion protein and linking it through the tag with an affinitive resin. From the fusion protein bonded to the affinitive resin, the objective enzyme protein can be isolated in various methods such as cleavage by protease like thrombin and blood coagulation factor Xa, lowering of pH, and addition of imidazole as a bonding competitive agent in a high concentration. Otherwise, when the tag contains "intein" by use of pTYB1 (produced by New England Biolab Co.) as the expression factor, the system is brought to a reductive condition to cleave the —S—S-bond. The fusion proteins which can be purified by affinity chromatography includes glutathione S-transferase (GST), chitin-bonded domain (CBD), maltose-bonded protein (MBP), and thioredoxin (TRX), in addition to the histidine tag. The GST fusion protein can be purified by GST-affinitive resin.

EXAMPLES

The present invention is described below more specifically by reference to Examples. The Examples below show best embodiments of the present invention without limiting the technical range of the present invention.

Reference Example 1

Preparation of Magnetic Particles

An aqueous solution containing ferrous hydroxide was prepared by adding, to an aqueous ferrous sulfate solution, a sodium hydroxide solution in an amount of 1.0-1.1 equivalent to the ferrous ion. Air was blown into this aqueous solution by keeping the pH of the aqueous solution at about 8 to cause oxidation reaction at 80-90° C. to obtain a liquid slurry for formation of seed crystals.

To this liquid slurry, was added an aqueous ferrous sulfate solution in an amount of 0.9-1.2 equivalent to the above added-alkali (the sodium of the above added sodium hydroxide), and air is blown therein to proceed an oxidation reaction by keeping the pH at about 8. The formed magnetic iron oxide particles after the oxidation reaction was collected by filtration, washed, and dried. The particulate iron oxide in an aggregating state was crushed to obtain magnetic particles (1) having an average particle size of 0.10 µm.

Example 1

Formation of Peptide Structure Capable of Linking to Magnetic substance

1. Preparation of Liquid Suspension of Magnetic Particles

To 5 mg of magnetic particle (1) prepared in Reference Example 1, was added 1 mL of a TBS buffer (50 mM tris-HCl (pH 7.5), 150 mM NaCl) to form a suspension. The suspension was centrifuged at 10,000 rpm (0.9300 g) for 5 minutes, and the supernatant was eliminated. The precipitate was suspended in 1 mL of acetone. The suspension was again centrifuged and the supernatant was eliminated under the same conditions as above. Further to the precipitate, was added 1 mL of a TBS-0.1T buffer (50 mM tris-HCl (pH 7.5), 150 mM NaCl, 0.1% Tween-20) to form a suspension. The suspension was centrifuged under the above conditions, and the supernatant was eliminated. This operation was repeated two more times. The obtained precipitate was suspended in 1 mL of a TBS-0.1T buffer. To 10 µL of the suspension, was added 990 µL of the TBS-0.1T buffer to prepare a magnetic particle liquid suspension for screening of the phage display peptide library.

2. Biopanning the Phage Display Peptide Library

To the above magnetic particle liquid suspension, were added 4×10$^{10}$ pfu of Ph.D.-12 phage display library (New England Biolabs, Inc.) and 100 µL of a TBS-0.1T buffer. The mixture was incubating for 30 minutes at room temperature (25° C.). Then the mixture was centrifuged at 10,000 (9300 g) for 5 minutes, and the supernatant was eliminated. The resulting precipitate was suspended in 1 mL of a TBS-0.1T buffer, the suspension was centrifuged at 10,000 rpm (9300 g) for 5 minutes, and the supernatant was eliminated. This washing treatment for elimination of the non-linked phage was repeated additionally 9 times. Thereafter the phage linked to the magnetic particles was recovered by a buffer of pH 2.2 (0.2 M glycine-HCl (pH 2.2), 1 mg/mL BSA). The recovered phage was allowed to infect *Escherichia coli* ER2537 for amplification.

This phage having been fractionated and amplified by the primary screening was subjected to secondary and successive screening. In the secondary and successive screening, the amount of the added phage was 2×10$^{11}$ pfu, and the buffer for the washing was a TBS-0.5T buffer (50 mM tris-HCl (pH 7.5), 150 mM NaCl, 0.5% Tween-20)

3. Sequencing of the DNA

After the above multi-step screening, a portion of the finally amplified phage was taken and subjected to cloning. From each of the isolated 35 clones, ssDNA was prepared respectively, and the base sequence in the random region in the peptide library was determined. From the coded base sequence in the random region, the corresponding amino acid sequences shown by SEQ ID NO:15 to SEQ ID NO:30 were selected as the amino acid sequence of the peptide capable of linking to the magnetic particles.

Example 2

Evaluation of Linkage of Magnet-Linking Peptide Structure to Magnetic substance A 5 μg portion of the magnetic fine particles prepared in Reference Example 1 was suspended in 100 μL of a TBS-0.1T buffer (50 mM tris-HCl (pH 7.5), 150 mM NaCl, 0.1% Tween 20). Thereto was added 10 μL of a solution containing $2 \times 10^{11}$ pfu of the phage having a peptide of the amino acid sequence SEQ ID NO:15. The mixture was agitated at room temperature (25° C.) for 30 minutes to cause linking reaction. Further it was suspended in TBS-0.5T buffer (50 mM tris-HCl (pH 7.5), 150 mM NaCl, 0.5% Tween 20), and was recovered by magnetic force. This treatment was repeated 10 times to release and wash off the non-adsorbed and non-specifically adsorbed phage.

According to the method described in Nature, 405, 665-668 (2000), the recovered magnetic fine particles containing specifically adsorbed phage were allowed to react with an anti-fd phage antibody-biotin complex (produced by Sigma Co.) and streptavidin-tetramethylrhodamine, and was recovered by magnetic force and was washed. This treatment was repeated three times in total. The magnetic fine particles were again dispersed in the aforementioned TBS-0.1T buffer.

The resulting liquid dispersion was observed by a incident-light microscope in a normal mode and in a fluorescence mode (excitation with green light by use of a filter). Thereby, the magnetic fine particles in the dispersion were observed to emit orange fluorescence caused by the rhodamine fluorochrome, which shows the presence of streptavidin-tetramethylrhodamine bonding to the anti-fd phage antibody-biotin complex.

For comparison, in place of the phage presenting the magnet-linking peptide selected by the above screening, the same amount of phage extracted arbitrarily from a random phage library was treated and observed for fluorescence in the same manner as above. Consequently, no fluorescence caused by the rhodamine fluorochrome was observed with the observed magnetic fine particles.

Further the linking experiments were conducted in the same manner by employing a phage presenting a magnet-linking peptide having an amino acid sequence of any of SEQ ID NO:16 to SEQ ID NO: 30. In any of the experiments, the orange fluorescence caused by the rhodamine flurochrome was observed to be emitted from the magnetic fine particles.

The above results show that through the peptide having the amino acid sequence selected by the screening in Example 1, the M13 phage presenting the peptide was immobilized by specific linkage on the magnetic fine particles.

Reference Example 2

Preparation of Transformant Capable of Producing PHA synthase, and Production of PHA synthase A transformant capable of producing a PHA synthase was prepared in a manner as below.

A *Pseudomonas cichorii* YN2 strain (hereinafter also referred to as "YN2") was cultivated in 100 mL of an LB medium (1% polypeptone, 0.5% yeast extract, 0.5% sodium chloride, pH 7.4) at 30° C. overnight. Then chromosomal DNA was isolated and recovered according to a Marmar's method. The obtained chromosomal DNA was completely cleaved by a restriction enzyme HindIII. pUC18 was employed as the cloning vector, which was cleaved by restriction enzyme HindIII. After dephosphorylation treatment of the terminal (Molecular Cloning, 1, 572, (1989); published by Cold Spring Harbor Laboratory), the complete decomposition fragments of chromosomal DNA by HindIII was linked and inserted into the cleavage site (cloning site) of the vector by use of a DNA ligation kit Ver. II (Takara Shuzo Co.). A DNA library of YN2 strain was prepared by transformation of *Escherichia coli* HB101 by use of the plasmid vector incorporating the above chromosomal DNA fragment.

Next, a colony hybridization probe was prepared for selection of DNA fragments containing PHA synthase chromosome derived from the YN2 strain. Oligonucleotide comprising the base sequences of SEQ ID NO:5 or SEQ ID NO:6 was synthesized (Amasham Pharmacia Biotech Co.). With these oligonucleotides as the primer, PCR amplification was conducted on a chromosomal DNA as the template. The DNA fragment formed by the PCR amplification was used as a probe for colony hybridization. The labeling of the probe was conducted by use of a commercial labeling enzyme system AlkPhosDirect (Amasham Pharmacia Biotech Co.). With the obtained labeled probe, an *Escherichia coli* strain having recombinant plasmid containing a PHA synthase gene was selected from the chromosomal DNA library of the YN2 strain by colony hybridization. From the selected bacteria strain, a DNA fragment containing PHA synthase gene was obtained by recovery of the plasmid by an alkali method.

The obtained gene DNA fragment was treated for recombination to vector pBBR122 (Mo Bi Tec) containing a large replication region in the host cell, not belonging to any of IncP, IncQ, and IncW which are incompatible. This recombinant plasmid was introduced into *Pseudomonas* cichorii YN2 ml (defective in PHA-synthesizing ability) by electroporation to cause transformation. As the result, the YN2 ml strain restored the PHA-synthesizing ability and became complementary. Thereby the selected gene DNA fragment was confirmed to contain a PHA synthase gene region which is capable of translation into a PHA synthase in the YN2 ml.

The base sequence of the DNA fragment containing the PHA synthase region was determined by a Sanger method. Thereby it was confirmed that the determined base sequence contained the base sequences SEQ ID NO:2 and SEQ ID NO:4 which codes respectively a peptide chain. As described below, the two proteins containing respectively the peptide chains coded as the above two base sequences have the enzymatic activity. Therefore, the base sequences SEQ ID NO:2 and SEQ ID NO:4 were confirmed to be a gene for coding a PHA synthase respectively. That is, the base sequence SEQ ID NO:2 codes the amino acid sequence represented by SEQ ID NO:1, and the base sequence SEQ ID NO:4 codes the amino acid sequence represented by SEQ ID NO:3. Each of the two proteins having the above amino acid sequence has the PHA-synthesizing ability.

The PHA synthase gene having the base sequence represented by SEQ ID NO:2 was subjected to PCR by employing the chromosomal DNA as the template to reproduce the entire length of the PHA synthase gene.

An oligonucleotide (SEQ ID NO:7) was designed and synthesized which has a base sequence of the upstream side of the initiation codon for the base sequence DEQ ID NO:2, and another oligonucleotide (SEQ ID NO:8) was also designed and synthesized which has a base sequence of the downstream side of the termination codon therefor (Amasham Pharmacia Biotech Co.). By employing these nucleotides as the primers, PCR was conducted to amplify the entire length of the PHA synthase gene (LA-PCR kit: Takara Shuzo Co.).

In the same manner, the PHA synthase gene having the base sequence represented by SEQ ID NO:4 was subjected to PCR by employing the chromosomal DNA as the template to reproduce the entire length of the PHA synthase gene. An oligonucleotide (SEQ ID NO:9) was designed and synthesized which has a base sequence of the upstream side of the initiation codon for the base sequence DEQ ID NO:4, and another oligonucleotide (SEQ ID NO:10) was also designed and synthesized which has a base sequence of the downstream side of the termination codon therefor (Amasham Pharmacia Biotech Co.). By employing these nucleotides as the primers, PCR was conducted to amplify the entire length of the PHA synthase gene (LA-PCR kit: Takara Shuzo Co.).

The two kinds of the resulting PCR amplified fragments comprising the entire length of the PHA synthase gene were cleaved completely by the restriction enzyme HindIII. The expression vector pTrc99A was also cleaved by the restriction enzyme HindIII, and was treated for dephosphorylation (Molecular Cloning, vol. 1, 572, 1989, published by cold Spring Harbor Laboratory). The DNA fragment from which unnecessary base sequences had been eliminated by digestion by the restriction enzyme HindIII and which has the complete length of the PHA synthase gene was ligated to the cleavage site of this expression vector pTrc99A by use of the DNA ligation kit Ver.II (Takara Shuzo Co.).

With the resulting recombinant plasmids, *Escherichia coli* was transformed by a calcium chloride method. The obtained recombinants were cultivated to amplify the recombinant plasmid. The recombinant plasmids were recovered. The recombinant plasmid holding the genetic DNA of SEQ ID NO:2 was named pYN2-C1 (originating from SEQ ID NO:2), and the recombinant plasmid holding the genetic DNA of SEQ ID NO:4 was named pYN2-C2 (originating from SEQ ID NO:4).

With the recombinant plasmids pYN2-C1 and pYN2-C2, *Escherichia coli* HB101fB (fadB defective strain) was transformed by a calcium chloride method to obtain a pYN2-C1 recombinant strain and a pYN2-C2 recombinant strain, each holding the respective recombinant plasmid.

The pYN2-C1 recombinant strain and the pYN2-C2 recombinant strain were inoculated respectively into 200 mL of M9 cultures containing 0.5% of yeast extract and 0.1% octanoic acid, and were cultivated at 37° C. with shaking at 125 stroke/min. After 24 hours of the cultivation, each bacteria mass was collected by centrifugation to recover the respective plasmid DNAs in a conventional manner.

For the plasmid pYN2-C1, an oligonucleotide (SEQ ID NO:11) as the upstream primer, and an oligonucleotide (SEQ ID NO:12) as the downstream primer were respectively designed and synthesized (Amasham Pharmacia Biotech.). By use of these nucleotides as the primers and the pYN2-C1 as the template, PCR was conducted to amplify the entire length of the PHA synthase gene having restriction sites of BamHI and SacI at the upstream side and restriction sites of SpeI and XhoI at the downstream side (LA-PCR kit, Takara Shuzo Co.).

In the same manner, for the plasmid pYN2-C2, an oligonucleotide (SEQ ID NO:13) as the upstream primer, and an oligonucleotide (SEQ ID NO:14) as the downstream primer were respectively designed and synthesized (Amasham Pharmacia Biotech Co.). By use of these nucleotides as the primers and the pYN2-C2 as the template, PCR was conducted to amplify the entire length of the PHA synthase gene having a restriction site of BamHI at the upstream side and a restriction site of XhoI at the downstream side (LA-PCR kit, Takara Shuzo Co.).

The purified PCR amplification products were respectively digested by BamHI and XhoI, and were inserted into corresponding sites of plasmid pGEX-6P-1 (Amasham Pharmacia Biotech. Co.). With these vectors (pGEX-C1 and pGEX-C2), *Escherichia coli*(JM109) was transformed to obtain an expression bacteria strain. The bacteria strain was confirmed by determining the base sequence of the DNA fragments formed by treatment of the plasmid prepared in a large amount with BamHI and XhoI by means of Miniprep (Wizard Minipreps DNA Purification Systems, produced by PROMEGA Co.). The obtained bacteria strain was pre-cultivated overnight in 10 mL of an LB-Amp culture. A 0.1 mL portion of the culture was added to 10 mL of an LB-Amp culture, and cultivated at 37° C. by shaking at 170 rpm for 3 hours. Thereto IPTG was added (final concentration: 1 mM) and the cultivation was continued at 37° C. for 4-12 hours. Incidentally, in the aforementioned expression vectors (pGEX-C1 and pGEX-C2), the PHA synthase gene is linked to the GST protein gene in a plasmid pGEX-6P-1, and is expressed as a GST fusion protein.

The *Escherichia coli* derived by addition of IPTG was collected by centrifugation (8000×g, 2 minutes, 4° C.). A 1/10 portion thereof was suspended again in PBS. The bacteria mass was crushed by freeze-thawing and sonication. Any solid contaminant was eliminated by centrifugation (8000×g, 10 minutes, 4° C.). After confirmation of the presence of the objective expression protein in the supernatant by SDS-PAGE, the GST fusion protein derived and expressed was purified by Glutathione Sepharose 4B (Glutathione Sepharose 4B Beads: produced by Amasham Pharmacia Biotech Co.).

Preliminarily, the glutathione-sepharose before use was treated for suppression of nonspecific adsorption as follows. The glutathione-sepharose was washed with an equal amount of PBS three times (8000×g, one minute, 4° C.), and treated with an equal amount of 4% BSA-containing PBS at 4° C. for one hour. The treated glutathione-sepharose was washed with an equal amount of PBS twice, and suspended again in half an amount of PBS. A 40 μL portion of the pretreated glutathione-sepharose was added to 1 mL of the cell-free liquid extract, and stirred gently at 4° C. Thereby, the fusion proteins GST-YN2-C1 and GST-YN-C2 were respectively adsorbed by the glutathione-sepharose.

After the adsorption, the glutathione-sepharose was recovered by centrifugation (8000×g, one minute, 4° C.) and washed with 400 μL of PBS three times. Thereto, 40 μL of 10 mM glutathione was added, and the mixture was stirred at 4° C. for one hour to elute the adsorbed fusion protein. The mixture was centrifuged (8000×g, two minutes, 4° C.) to recover the supernatant. The recovered supernatant was dialyzed by use of PBS to purify the GST fusion protein. After the purification, the protein was confirmed to show a single band in SDS-PAGE analysis.

A 500 μg portion of each of the GST fusion proteins was digested by PreScission protease (Amasham Pharmacia Biotech Co., 5U). The digested mixture was allowed to flow through a glutathione-sepharose to remove the protease and the GST. The flow-through fraction containing the PHA synthase was allowed to flow though a Sephadex G200 column having been equilibrated with PBS. Thus final purified products of recombinant expression proteins YN2-C1 and YN2-C2 were obtained. The proteins were confirmed to show respectively a single band in SDS-PAGE at 60.8 kDa, and 61.5 kDa.

The enzymatic activity of each of the purified PHA synthases was measured by causing 3-hydroxyacyl CoA polymerization by the enzyme to synthesize PHA. The activity is represented by the amount of CoA released in the PHA synthesis reaction, taking the amount of PHA synthase for releasing 1 mmol of CoA per minute as one unit (U). The protein concentration in the test sample was measured with a MicroBCA Protein Determination Reagent Kit (produced by Pias Chemical Co.). Table 1 shows the measured activities of the respective purified enzymes.

TABLE 1

| Activities of Polyhydroxyalkanoate-Synthesizing Enzyme | | |
|---|---|---|
| Enzyme | Activity | Specific activity |
| YN2—C1 | 2.1 U/mL | 4.1 U/mg-protein |
| YN2—C2 | 1.5 U/mL | 3.6 U/mg-protein |

The respective purified enzyme solution was concentrated by use of a biosubstance solution-concentrating agent (Mizubutorikun AB-1100, produced by Atoh K.K.) to obtain a purified enzyme solution having an activity of 10 U/mL.

Example 3

Preparation of Fusion protein of Magnet-Linking Peptide and PHA synthase

An *E. coli*-expressing vector was constructed which expresses a fusion protein of a magnet-linking peptide and a PHA synthase in which a magnet-linking amino acid sequence SEQ ID NO:15 is fused through a linker sequence SEQ ID NO:38 with an N-terminal of PHA synthase amino acid sequence in a procedure shown below. The DNA for coding the magnet-linking sequence and the linker sequence portion is prepared as a double-stranded synthesizing oligonucleotide, and is ligated to a suitable restricted cleavage site (BamHI and SacI) of plasmid pGEX-C1 plasmid for expressing a fusion protein GST-YN2-C1. In this operation, according to the instruction given by the maker, two synthesized oligonucleotides O1 (SEQ ID NO: 31) and O2 (SEQ ID NO:32) were phosphorylated by use of T4 polynucleotide-kinase (produced by Gibco Co.). Subsequently, the obtained products were cooled slowly to room temperature. The resulting double-stranded DNA fragments were used directly for the cloning.

The plasmid pGEX-C1 was digested by BamHI and SacI, and thereto the above double-stranded DNA fragments were inserted. With this vector, *Escherichia coli* (JM109) was transformed into an expression bacteria. The bacteria strain was confirmed by sequencing the base sequence of the insert with pGEX 5' Sequencing Primer (Amasham Pharmacia Biotech Co.) by employing as the template a plasmid DNA prepared by use of Miniprep (Wizard Minipreps DNA Purification Systems, produced by PROMEGA Co.). The obtained bacteria was cultivated preliminarily in 10 mL of an LB-Amp culture medium. A 0.1 mL of this liquid culture was added to 10 mL of an LB-Amp culture medium, and cultivated at 37° C. with shaking at 170 rpm for 3 hours. Thereto IPTG was added (final concentration: 1 mM), and the cultivation was continued at 37° C. for 4-12 hours. In the resulting expression vector, GST fusion protein was coded for the linkage in the order of the fusion partner protein GST, the magnetic-linking sequence and the linker sequence, and the PHA synthase YN2-C1.

The *Escherichia coli* derived by addition of IPTG was collected by centrifugation (8000×g, 2 minutes, 4° C.). A ¹⁄₁₀ portion thereof was suspended again in a PBS. The bacteria mass was crushed by freeze-thawing and sonication. Any solid contaminant was eliminated by centrifugation (8000× g, 10 minutes, 4° C.). After confirmation of the presence of the objective expression protein in the supernatant by SDS-PAGE, the GST-fusion protein derived and expressed was purified with Glutathione Sepharose 4B (Glutathione Sepharose 4B Beads: produced by Amasham Pharmacia Biotech Co.).

Preliminarily, the glutathione-sepharose before use was treated for suppression of nonspecific adsorption as follows. The glutathione-sepharose was washed with an equal amount of PBS three times (8000×g, one minute, 4° C.), and treated with an equal amount of 4% BSA-containing PBS at 4° C. for one hour. The treated glutathione-sepharose was washed with an equal amount of PBS twice, and suspended again in half an amount of PBS.

A 40 μL portion of the pretreated glutathione-sepharose was added to 1 mL of the cell-free extract, and stirred gently at 4° C. Thereby, the fusion protein GST-(magnet-linking peptide+linker peptide)-YN2-C1 was adsorbed by the glutathione-sepharose.

After the adsorption, the glutathione-sepharose was recovered by centrifugation (8000×g, one minute, 4° C.) and washed with 400 μL portions of PBS three times. Thereto, 40 μL of 10 mM glutathione was added, and the mixture was stirred at 4° C. for one hour to elute the adsorbed GST fusion protein. The mixture was centrifuged (8000×g, two minutes, 4° C.) to recover the supernatant. The recovered supernatant was dialyzed by use of PBS to purify the GST fusion protein. After the purification, the protein was confirmed to show a single band in SDS-PAGE analysis.

A 500 μg portion of the purified GST fusion protein was digested by PreScission protease (Amasham Pharmacia Biotech Co. 5U). The digested mixture was allowed to flow through a glutathione-sepharose to remove the protease and the GST. The flow-through fraction was further allowed to flow though a Sephadex G200 column having been equilibrated with PBS. The obtained final purified product was a recombinant expression protein YN2-C1(Fe)15 of a type of a complex of a magnet-linking peptide PHA synthase. The protein was confirmed to show a single band in SDS-PAGE at 61.9 kDa.

The enzymatic activity of the purified enzyme was measured in the same manner as in Example 2. The protein concentration in the test sample was measured with a MicroBCA Protein Determination Reagent kit (produced by Pias Chemical Co.). The enzyme activity was found to be 1.9 U/mL, and the specific activity was 4.0 U/mg protein. The purified enzyme solution was concentrated by use of a biosubstance solution-concentrating agent (Mizubutorikun AB-1100, produced by Atoh K.K.) to obtain a purified enzyme solution having an activity of 10 U/mL.

In this Example, BamHI and SacI were used as the restriction enzyme. In the same manner, by use of Spec I and XhoI, an expression vector of *Escherichia coli* can be constructed which expresses a complex of a magnet-linking peptide and PHA synthase by employing SEQ ID NO:33 and SEQ ID NO:34. Similarly by using suitable sequence of synthesizing oligonucleotide, vectors having an amino acid sequence selected from sequence 16-30 can be constructed.

Example 4

Evaluation of ability of Fusion protein of Magnet-Linking Peptide and HPA-Synthesizing Enzyme for Linking with Magnetic substance Fine particulate magnetic substance was suspended at a concentration of 0.5% (w/v) in a TBS buffer containing 0.1% Tween-20. A 10 mL portion of this liquid suspension was placed in a centrifuging teflon tube. Thereto were added the enzyme protein YN2-C1(Fe)15 of a type of the fusion protein, prepared in Example 3, of a magnet-linking peptide and a PHA synthase in an amount corresponding to 0.5 U. The mixture was shaken at room temperature for 30 minutes.

From the suspension after the reaction, the magnetic particles were recovered as precipitate by magnetic force to separate the supernatant containing the enzyme not linking to the magnetic particles. The recovered magnetic particles were suspended again in a TBS buffer containing 0.1% Tween-20, and recovered by magnetic force for washing. The washing operation was repeated.

After the washing, the enzyme activity of the recovered magnetic substance suspension was measured.

The enzyme protein YN2-C1 prepared in Reference Example 2 was tested in the same manner as above.

Table 2 shows the measured enzyme activities.

TABLE 2

| Ability of PHA synthase to Link to Ferrite | |
|---|---|
| Enzyme | Activity (U) |
| YN2—C1(Fe)15 | 0.12 |
| YN2—C1 | 0.01 |

Fusion proteins of the magnet-linking peptide and the PHA synthase (YN2-C1(Fe)16 to YN2-C1(Fe)30) were prepared also by employing 15 magnet-linking sequences, SEQ ID NO:16 to SEQ ID NO:30, and were evaluated for ability of linking to the magnetic substance by measuring the PHA synthase activity for linking to the magnetic substance. Table 3 shows the results.

TABLE 3

| Ability of PHA synthase to Link to Ferrite | |
|---|---|
| Enzyme | Activity (U) |
| YN2—C1(Fe)16 | 0.11 |
| YN2—C1(Fe)17 | 0.10 |
| YN2—C1(Fe)18 | 0.12 |
| YN2—C1(Fe)19 | 0.09 |
| YN2—C1(Fe)20 | 0.09 |
| YN2—C1(Fe)21 | 0.09 |
| YN2—C1(Fe)22 | 0.12 |
| YN2—C1(Fe)23 | 0.10 |
| YN2—C1(Fe)24 | 0.11 |
| YN2—C1(Fe)25 | 0.10 |
| YN2—C1(Fe)26 | 0.12 |
| YN2—C1(Fe)27 | 0.12 |
| YN2—C1(Fe)28 | 0.12 |
| YN2—C1(Fe)29 | 0.11 |
| YN2—C1(Fe)30 | 0.09 |
| YN2—C1 | 0.01 |

The magnetic substances brought into contact with one of the enzymes, YN2-C1(Fe)16 to YN2-C1(Fe)30, which are fused with a magnet-linking sequence had high enzyme activity in comparison with the control brought into contact with the enzyme, YN2-C1, which contains no magnet-linking sequence. This means that the enzyme in a state of a complex of magnet-linking peptide and PHA synthase can be immobilized on the magnetic substance effectively.

Example 5

Evaluation of Linking Ability of Joined Two-Peptide to Magnetic substance

An *E. coli* expression vector for expressing a complex was constructed: the complex being constituted by combining two amino acid sequences, SEQ ID NO:15 and SEQ ID NO:16, capable of linking to a magnetic substance, through a linker sequence SEQ ID NO:39 in this order in series to form a sequence SEQ ID NO:35, and further by combining this sequence through a linker sequence GS to an N-terminal of a PHA synthase. The construction was conducted specifically as below. The DNA for coding the amino acid sequence to be joined to the N-terminal of the PHA synthase was formed by phosphorylating two synthetic oligonucleotides, SEQ ID NO:36 and SEQ ID NO:37, respectively with a T4 polynucleotide kinase (produced by Gibco Co.), mixing the products in equimolar amounts, heating the mixture at 80° C. for 5 minutes, and cooling it slowly to room temperature to form a double-stranded DNA fragment. The formed double-stranded DNA fragment was inserted into BamHI/SacI site of the plasmid pGEX, and with this vector, *Escherichia coli* (JM109) was transformed into a bacteria strain for expression in the same manner as Example 3. The expression protein YN-C1(Fe)95 obtained by fusing the amino acid sequence SEQ ID NO:35 to the N-terminal was purified in the same manner as in Example 3 to obtain a purified enzyme solution having activity of 10 U/mL. The ability of linking to the magnetic substance was evaluated in the same manner as in Example 4. Table 4 shows the evaluation result.

TABLE 4

| Ability of Polyhydroxyalkanoate-Synthesizing Enzyme to Link to Ferrite | |
|---|---|
| Enzyme | Activity (U) |
| YN2—C1(Fe)95 | 0.11 |
| YN2—C1 | 0.01 |

The magnetic substances brought into contact with the enzymes, YN2-C1(Fe)$_{95}$, which are fused with a magnet-linking sequence had high enzyme activity in comparison with the control brought into contact with the enzyme, YN2-C1, which does not contain the magnet-linking sequence. This means that the enzyme can be immobilized on the magnetic substance effectively in a form of a complex of a magnet-linking peptide and PHA synthase (aaa147-YN2-C1(cb): YN2-C1(Fe)$_{95}$).

The invention claimed is:

1. A peptide fragment that binds to a magnetic substance comprising: SEQ ID NO:15 as an amino acid sequence.

2. A DNA sequence encoding a peptide fragment that binds to a magnetic substance, the peptide fragment comprising: SEQ ID NO:15 as an amino acid sequence.

* * * * *

UNITED STATES PATENT AND TRADEMARK OFFICE
CERTIFICATE OF CORRECTION

PATENT NO. : 7,354,995 B2
APPLICATION NO. : 10/546404
DATED : April 8, 2008
INVENTOR(S) : Takeshi Imamura et al.

It is certified that error appears in the above-identified patent and that said Letters Patent is hereby corrected as shown below:

ON TITLE PAGE [56] REFERENCES CITED:

Other Publications, (insert)
--Sambrook et al., "Molecular Cloning," 2$^{nd}$ ed., Published by Cold Spring Harbor Laboratory Press, 5.72 (1989).

Klauser et al., "Extracellular Transport of Cholera Toxin B Subunit Using Neisseria IgA Protease β-domain: Conformation-Dependent Outer Membrane Translocation," EMBO J., vol. 9, pp. 1991-1999 (1990).

Scott et al., "Searching for Peptide Ligands with an Epitope Library," Science, vol. 249, pp. 386-390 (1990).

Cwirla et al., "Peptides on Phage: A Vast Library of Peptides for Identifying Ligands," Proc. Natl. Acad. Sci. USA, vol. 87, pp. 6378-6382 (1990).

Hofnung, Maurice, "Expression of Foreign Polypeptides at the Escherichia Coli Cell Surface," Methods in Cell Biology, vol. 34, pp. 78-105 (1991).

Fodor et al., "Light-Directed, Spatially Addressable Parallel Chemical Synthesis," Science, vol. 251, pp. 767-773 (1991).--.

COLUMN 3:

Line 6, "Magnetic" should read --magnetic--.

COLUMN 7:

Line 29, "fusion-body" should read --fusion body--.

COLUMN 8:

Line 7, "methods" should read --method.--.

COLUMN 19:

Line 42, "$O_2$" should read --O2--.

UNITED STATES PATENT AND TRADEMARK OFFICE
CERTIFICATE OF CORRECTION

PATENT NO.         : 7,354,995 B2
APPLICATION NO. : 10/546404
DATED               : April 8, 2008
INVENTOR(S)      : Takeshi Imamura et al.

It is certified that error appears in the above-identified patent and that said Letters Patent is hereby corrected as shown below:

COLUMN 22:

Line 59, "YN2-Cl(Fe)$_{95,}$" should read --YN2-Cl(Fe)95,--; and
Line 66, "YN2-Cl(Fe)$_{95}$)." should read --YN2-Cl(Fe)95).--.

Signed and Sealed this

Fourteenth Day of October, 2008

JON W. DUDAS
*Director of the United States Patent and Trademark Office*

SEQUENCE LISTING

<160> NUMBER OF SEQ ID NOS: 39

<210> SEQ ID NO 1
<211> LENGTH: 559
<212> TYPE: PRT
<213> ORGANISM: Pseudomonas cichorii YN2; FERM BP-7375

<400> SEQUENCE: 1

```
Met Ser Asn Lys Ser Asn Asp Glu Leu Lys Tyr Gln Ala Ser Glu Asn
1               5                   10                  15

Thr Leu Gly Leu Asn Pro Val Val Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
```

```
                355                 360                 365
Met Arg Pro Asn Asp Leu Ile Trp Asn Tyr Trp Val Asn Asn Tyr Leu
        370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
                420                 425                 430

Pro Ile Asp Leu Lys Gln Val Thr Ala Asp Ile Phe Ser Leu Ala Gly
                435                 440                 445

Thr Asn Asp His Ile Thr Pro Trp Lys Ser Cys Tyr Lys Ser Ala Gln
        450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
                500                 505                 510

Lys His Thr Asp Ser Trp Trp Leu His Trp Gln Ala Trp Gln Ala Gln
        515                 520                 525

Arg Ser Gly Glu Leu Lys Lys Ser Pro Thr Lys Leu Gly Ser Lys Ala
        530                 535                 540

Tyr Pro Ala Gly Glu Ala Ala Pro Gly Thr Tyr Val His Glu Arg
545                 550                 555

<210> SEQ ID NO 2
<211> LENGTH: 1680
<212> TYPE: DNA
<213> ORGANISM: Pseudomonas cichorii YN2; FERM BP-7375

<400> SEQUENCE: 2
atgagtaaca agagtaacga tgagttgaag tatcaagcct ctgaaaacac cttggggctt     60
aatcctgtcg ttgggctgcg tggaaaggat ctactggctt ctgctcgaat ggtgcttagg    120
caggccatca gcaaccggt gcacagcgtc aaacatgtcg cgcactttgg tcttgaactc     180
aagaacgtac tgctgggtaa atccgggctg caaccgacca gcgatgaccg tcgcttcgcc    240
gatccggcct ggagccagaa cccgctctat aaacgttatt tgcaaaccta cctggcgtgg    300
cgcaaggaac tccacgactg gatcgatgaa agtaacctcg cccccaagga tgtggcgcgt    360
gggcacttcg tgatcaacct catgaccgaa gccatggcgc cgaccaacac cgcggccaac    420
ccggcggcag tcaaacgctt tttcgaaacc ggtggcaaaa gctgctcga cggcctctcg    480
cacctggcca aggatctggt acacaacggc ggcatgccga gccaggtcaa catgggtgca    540
ttcgaggtcg gcaagagcct gggcgtgacc gaaggcgcgg tggtgtttcg caacgatgtg    600
ctggaactga tccagtacaa gccgaccacc gagcaggtat acgaacgccc gctgctggtg    660
gtgccgccgc agatcaacaa gttctacgtt ttcgacctga gccggacaa gagcctggcg    720
cggttctgcc tgcgcaacaa cgtgcaaacg ttcatcgtca gctggcgaaa tcccaccaag    780
gaacagcgag agtggggcct gtcgacctac atcgaagccc tcaaggaagc ggttgatgtc    840
gttaccgcga tcaccggcag caaagacgtg aacatgctcg gcgcctgctc cggcggcatc    900
acttgcaccg cgctgctggg ccattacgcg gcgattggcg aaaacaaggt caacgccctg    960
accttgctgg tgagcgtgct tgataccacc ctcgacagcg atgttgccct gttcgtcaat   1020
```

```
gaacagaccc ttgaagccgc caagcgccac tcgtaccagg ccggcgtact ggaaggccgc   1080
gacatggcga aggtcttcgc ctggatgcgc cccaacgatc tgatctggaa ctactgggtc   1140
aacaattacc tgctaggcaa cgaaccgccg gtgttcgaca tcctgttctg gaacaacgac   1200
accacacggt tgcccgcggc gttccacggc gacctgatcg aactgttcaa aaataaccca   1260
ctgattcgcc cgaatgcact ggaagtgtgc ggcaccccca tcgacctcaa gcaggtgacg   1320
gccgacatct tttccctggc cggcaccaac gaccacatca ccccgtggaa gtcctgctac   1380
aagtcggcgc aactgtttgg cggcaacgtt gaattcgtgc tgtcgagcag cgggcatatc   1440
cagagcatcc tgaacccgcc gggcaatccg aaatcgcgct acatgaccag caccgaagtg   1500
gcggaaaatg ccgatgaatg caagcgaat gccaccaagc ataccgattc ctggtggctg    1560
cactggcagg cctggcaggc ccaacgctcg ggcgagctga aaaagtcccc gacaaaactg   1620
ggcagcaagg cgtatccggc aggtgaagcg gcgccaggca cgtacgtgca cgaacggtaa   1680
```

```
<210> SEQ ID NO 3
<211> LENGTH: 560
<212> TYPE: PRT
<213> ORGANISM: Pseudomonas cichorii YN2; FERM BP-7375

<400> SEQUENCE: 3

Met Arg Asp Lys Pro Ala Arg Glu Ser Leu Pro Thr Pro Ala Lys Phe
1               5                   10                  15

Ile Asn Ala Gln Ser Ala Ile Thr Gly Leu Arg Gly Arg Asp Leu Val
            20                  25                  30

Ser Thr Leu Arg Ser Val Ala Ala His Gly Leu Arg His Pro Val His
        35                  40                  45

Thr Ala Arg His Ala Leu Lys Leu Gly Gly Gln Leu Gly Arg Val Leu
    50                  55                  60

Leu Gly Asp Thr Leu His Pro Thr Asn Pro Gln Asp Arg Arg Phe Asp
65                  70                  75                  80

Asp Pro Ala Trp Ser Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
        115                 120                 125

Asn Asp Ala Val Ser Pro Ser Asn Ser Leu Leu Asn Pro Leu Ala Ile
    130                 135                 140

Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Arg His Ala Phe Glu Val Gly Lys Thr Val Ala Thr Thr Thr Gly
            180                 185                 190

Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
    210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255
```

```
Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415

Phe Lys His Asn Pro Leu Ser His Pro Gly Gly Leu Glu Val Cys Gly
            420                 425                 430

Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
    450                 455                 460

Leu Leu Leu Gly Gly Glu Arg Arg Phe Val Leu Ala Asn Ser Gly His
465                 470                 475                 480

Val Gln Ser Ile Leu Asn Pro Pro Asn Asn Pro Lys Ala Asn Tyr Leu
                485                 490                 495

Glu Gly Ala Lys Leu Ser Ser Asp Pro Arg Ala Trp Tyr Tyr Asp Ala
            500                 505                 510

Lys Pro Val Asp Gly Ser Trp Trp Thr Gln Trp Leu Gly Trp Ile Gln
        515                 520                 525

Glu Arg Ser Gly Ala Gln Lys Glu Thr His Met Ala Leu Gly Asn Gln
    530                 535                 540

Asn Tyr Pro Pro Met Glu Ala Ala Pro Gly Thr Tyr Val Arg Val Arg
545                 550                 555                 560

<210> SEQ ID NO 4
<211> LENGTH: 1683
<212> TYPE: DNA
<213> ORGANISM: Pseudomonas cichorii YN2; FERM BP-7375

<400> SEQUENCE: 4
atgcgcgata aacctgcgag ggagtcacta cccaccccg ccaagttcat caacgcacaa      60
agtgcgatta ccggcctgcg tggccgggat ctggtttcga cttttgcgcag tgtcgccgcc    120 catggcctgc gccaccccgt gcacaccgcg cgacacgcct tgaaactggg tggtcaactg    180
ggacgcgtgt tgctgggcga caccctgcat cccaccaacc gcaagaccg tcgcttcgac     240 gatccggcgt ggagtctcaa tccctttttat cgtcgcagcc tgcaggcgta cctgagctgg    300
cagaagcagg tcaagagctg gatcgacgaa agcaacatga gcccggatga ccgcgcccgt    360
gcgcacttcg cgttcgccct gctcaacgat gccgtgtcgc cgtccaacag cctgctcaat    420
```

-continued

| | |
|---|---|
| ccgctggcga tcaaggaaat cttcaactcc ggcggcaaca gcctggtgcg cgggatcggc | 480 |
| catctggtcg atgacctctt gcacaacgat ggcttgcccc ggcaagtcac caggcatgca | 540 |
| ttcgaggttg gcaagaccgt cgccaccacc accggcgccg tggtgtttcg caacgagctg | 600 |
| ctggagctga tccaatacaa gccgatgagc gaaaagcagt attccaaacc gctgctggtg | 660 |
| gtgccgccac agatcaacaa gtactacatt tttgacctca gcccccataa cagcttcgtc | 720 |
| cagttcgcgc tcaagaacgg cctgcaaacc ttcgtcatca gctggcgcaa tccggatgta | 780 |
| cgtcaccgcg aatggggcct gtcgacctac gtcgaagcgg tggaagaagc catgaatgtc | 840 |
| tgccgggcaa tcaccggcgc gcgcgaggtc aacctgatgg gcgcctgcgc tggcgggctg | 900 |
| accattgctg ccctgcaggg ccacttgcaa gccaagcgac agctgcgccg cgtctccagc | 960 |
| gcgacgtacc tggtgagcct gctcgacagc caactggaca gcccggccac actcttcgcc | 1020 |
| gacgaacaga ccctggaggc ggccaagcgc cgctcctacc agaaaggtgt gctggaaggc | 1080 |
| cgcgacatgg ccaaggtttt cgcctggatg cgccccaacg atttgatctg gagctacttc | 1140 |
| gtcaacaatt acctgatggg caaggagccg ccggcgttcg acattctcta ctggaacaat | 1200 |
| gacaacacac gcctgccggc cgccctgcat ggtgacttgc tggacttctt caagcacaac | 1260 |
| ccgctgagcc atccgggtgg cctggaagtg tgcggcaccc cgatcgactt gcaaaaggtc | 1320 |
| accgtcgaca gtttcagcgt ggccggcatc aacgatcaca tcacgccgtg ggacgcggtg | 1380 |
| tatcgctcaa ccctgttgct cggtggcgag cgtcgctttg tcctggccaa cagcggtcat | 1440 |
| gtgcagagca ttctcaaccc gccgaacaat ccgaaagcca actacctcga aggtgcaaaa | 1500 |
| ctaagcagcg accccagggc ctggtactac gacgccaagc ccgtcgacgg tagctggtgg | 1560 |
| acgcaatggc tgggctggat tcaggagcgc tcgggcgcgc aaaaagaaac ccacatggcc | 1620 |
| ctcggcaatc agaattatcc accgatggag gcggcgcccg ggacttacgt gcgcgtgcgc | 1680 |
| tga | 1683 |

<210> SEQ ID NO 5
<211> LENGTH: 20
<212> TYPE: DNA
<213> ORGANISM: Artificial
<220> FEATURE:
<223> OTHER INFORMATION: Primer for PCR multiplication

<400> SEQUENCE: 5
tgctggaact gatccagtac                                            20

<210> SEQ ID NO 6
<211> LENGTH: 23
<212> TYPE: DNA
<213> ORGANISM: Artificial
<220> FEATURE:
<223> OTHER INFORMATION: Primer for PCR multiplication

<400> SEQUENCE: 6
gggttgagga tgctctggat gtg                                        23

<210> SEQ ID NO 7
<211> LENGTH: 29
<212> TYPE: DNA
<213> ORGANISM: Artificial
<220> FEATURE:
<223> OTHER INFORMATION: Primer for PCR multiplication

<400> SEQUENCE: 7
ggaccaagct tctcgtctca gggcaatgg                                  29

<210> SEQ ID NO 8
<211> LENGTH: 29
<212> TYPE: DNA
<213> ORGANISM: Artificial
<220> FEATURE:
<223> OTHER INFORMATION: Primer for RCR multiplication

<400> SEQUENCE: 8
cgagcaagct tgctcctaca ggtgaaggc                                29

<210> SEQ ID NO 9
<211> LENGTH: 29
<212> TYPE: DNA
<213> ORGANISM: Artificial
<220> FEATURE:
<223> OTHER INFORMATION: Primer for PCR multiplication

<400> SEQUENCE: 9
gtattaagct tgaagacgaa ggagtgttg                                29

<210> SEQ ID NO 10
<211> LENGTH: 30
<212> TYPE: DNA
<213> ORGANISM: Artificial
<220> FEATURE:
<223> OTHER INFORMATION: Primer for PCR multiplication

<400> SEQUENCE: 10
catccaagct tcttatgatc gggtcatgcc                               30

<210> SEQ ID NO 11
<211> LENGTH: 45
<212> TYPE: DNA
<213> ORGANISM: Artificial
<220> FEATURE:
<223> OTHER INFORMATION: Primer for PCR multiplication

<400> SEQUENCE: 11
agtggatcct ccgagctcag taacaagagt aacgatgagt tgaag              45

<210> SEQ ID NO 12
<211> LENGTH: 45
<212> TYPE: DNA
<213> ORGANISM: Artificial
<220> FEATURE:
<223> OTHER INFORMATION: Primer for PCR multiplication

<400> SEQUENCE: 12
atactcgaga ctactagtcc gttcgtgcac gtacgtgcct ggcgc              45

<210> SEQ ID NO 13
<211> LENGTH: 45
<212> TYPE: DNA
<213> ORGANISM: Artificial
<220> FEATURE:
<223> OTHER INFORMATION: Primer for PCR multiplication

<400> SEQUENCE: 13
agtggatcct ccgagctccg cgataaacct gcgagggagt cacta              45

<210> SEQ ID NO 14
<211> LENGTH: 45
<212> TYPE: DNA
<213> ORGANISM: Artificial
<220> FEATURE:

-continued

<223> OTHER INFORMATION: Primer for PCR multiplication

<400> SEQUENCE: 14
atactcgaga ctactagtgc gcacgcgcac gtaagtcccg ggcgc            45

<210> SEQ ID NO 15
<211> LENGTH: 12
<212> TYPE: PRT
<213> ORGANISM: Artificial
<220> FEATURE:
<223> OTHER INFORMATION: Ferrite-binding peptide

<400> SEQUENCE: 15

Met Pro Ser Trp Arg Thr His His Val Ala Thr Pro
1               5                   10

<210> SEQ ID NO 16
<211> LENGTH: 12
<212> TYPE: PRT
<213> ORGANISM: Artificial
<220> FEATURE:
<223> OTHER INFORMATION: Ferrite-binding peptide

<400> SEQUENCE: 16

Met Gln Thr His His Thr Thr Val Thr Ser Trp Thr
1               5                   10

<210> SEQ ID NO 17
<211> LENGTH: 12
<212> TYPE: PRT
<213> ORGANISM: Artificial
<220> FEATURE:
<223> OTHER INFORMATION: Ferrite-binding peptide

<400> SEQUENCE: 17

Met Leu Pro His Arg Pro Pro His Tyr Met Ser His
1               5                   10

<210> SEQ ID NO 18
<211> LENGTH: 12
<212> TYPE: PRT
<213> ORGANISM: Artificial
<220> FEATURE:
<223> OTHER INFORMATION: Ferrite-binding peptide

<400> SEQUENCE: 18

Met Leu Asn Pro Pro Gln Gly His His His Met Gly
1               5                   10

<210> SEQ ID NO 19
<211> LENGTH: 12
<212> TYPE: PRT
<213> ORGANISM: Artificial
<220> FEATURE:
<223> OTHER INFORMATION: Ferrite-binding peptide

<400> SEQUENCE: 19

His Thr Met His Ala Trp Pro Pro Ala Pro Phe
1               5                   10

<210> SEQ ID NO 20
<211> LENGTH: 12
<212> TYPE: PRT
<213> ORGANISM: Artificial
<220> FEATURE:
<223> OTHER INFORMATION: Ferrite-binding peptide

```
<400> SEQUENCE: 20

His Ala His His Gln Gln His Leu Lys Pro Gln Ser
1               5                   10

<210> SEQ ID NO 21
<211> LENGTH: 12
<212> TYPE: PRT
<213> ORGANISM: Artificial
<220> FEATURE:
<223> OTHER INFORMATION: Ferrite-binding peptide

<400> SEQUENCE: 21

Gly Leu Asp Ser Gly Pro Thr His Arg His Met Phe
1               5                   10

<210> SEQ ID NO 22
<211> LENGTH: 12
<212> TYPE: PRT
<213> ORGANISM: Artificial
<220> FEATURE:
<223> OTHER INFORMATION: Ferrite-binding peptide

<400> SEQUENCE: 22

Gly Tyr Ala Ser Pro Lys Ala His Trp Ser Ser Gly
1               5                   10

<210> SEQ ID NO 23
<211> LENGTH: 12
<212> TYPE: PRT
<213> ORGANISM: Artificial
<220> FEATURE:
<223> OTHER INFORMATION: Ferrite-binding peptide

<400> SEQUENCE: 23

Ala Ser Arg Pro Met His Met Pro His Ile Pro Ala
1               5                   10

<210> SEQ ID NO 24
<211> LENGTH: 12
<212> TYPE: PRT
<213> ORGANISM: Artificial
<220> FEATURE:
<223> OTHER INFORMATION: Ferrite-binding peptide

<400> SEQUENCE: 24

Ala Pro Gly Met Asn Ala Met Ala Ser Ile His His
1               5                   10

<210> SEQ ID NO 25
<211> LENGTH: 12
<212> TYPE: PRT
<213> ORGANISM: Artificial
<220> FEATURE:
<223> OTHER INFORMATION: Ferrite-binding peptide

<400> SEQUENCE: 25

His Asn His Gln Phe Gln Ala Ser Met His Pro Asp
1               5                   10

<210> SEQ ID NO 26
<211> LENGTH: 12
<212> TYPE: PRT
<213> ORGANISM: Artificial
<220> FEATURE:
<223> OTHER INFORMATION: Ferrite-binding peptide

<400> SEQUENCE: 26
```

-continued

Arg Ser Ile His His Asp Ser His Met Leu Arg Gly
1               5                   10

<210> SEQ ID NO 27
<211> LENGTH: 12
<212> TYPE: PRT
<213> ORGANISM: Artificial
<220> FEATURE:
<223> OTHER INFORMATION: Ferrite-binding peptide

<400> SEQUENCE: 27

Thr His Ser Asn Ser Met Thr Arg Asn Thr Pro Met
1               5                   10

<210> SEQ ID NO 28
<211> LENGTH: 12
<212> TYPE: PRT
<213> ORGANISM: Artificial
<220> FEATURE:
<223> OTHER INFORMATION: Ferrite-binding peptide

<400> SEQUENCE: 28

Gly Leu Asp Ser Gly Pro Thr His Arg His Met Phe
1               5                   10

<210> SEQ ID NO 29
<211> LENGTH: 12
<212> TYPE: PRT
<213> ORGANISM: Artificial
<220> FEATURE:
<223> OTHER INFORMATION: Ferrite-binding peptide

<400> SEQUENCE: 29

Asp Gly His Gln Pro Phe His Thr Leu Lys Pro Ala
1               5                   10

<210> SEQ ID NO 30
<211> LENGTH: 12
<212> TYPE: PRT
<213> ORGANISM: Artificial
<220> FEATURE:
<223> OTHER INFORMATION: Ferrite-binding peptide

<400> SEQUENCE: 30

Gln Glu Ser His Gly Gly Pro Pro Arg Ser Pro His
1               5                   10

<210> SEQ ID NO 31
<211> LENGTH: 58
<212> TYPE: DNA
<213> ORGANISM: Artificial
<220> FEATURE:
<223> OTHER INFORMATION: Primer for PCR multiplication

<400> SEQUENCE: 31
gatccatgcc gagttggagg actcatcatg ttgcgactcc gggtggaggt tcggagct         58

<210> SEQ ID NO 32
<211> LENGTH: 50
<212> TYPE: DNA
<213> ORGANISM: Artificial
<220> FEATURE:
<223> OTHER INFORMATION: Primer for PCR multiplication

<400> SEQUENCE: 32
ccgaacctcc acccggagtc gcaacatgat gagtcctcca actcggcatg                  50

<210> SEQ ID NO 33
<211> LENGTH: 54
<212> TYPE: DNA
<213> ORGANISM: Artificial
<220> FEATURE:
<223> OTHER INFORMATION: Primer for PCR multiplication

<400> SEQUENCE: 33
ctagtatgcc gagttggagg actcatcatg ttgcgactcc gggtggaggt tcgc      54

<210> SEQ ID NO 34
<211> LENGTH: 54
<212> TYPE: DNA
<213> ORGANISM: Artificial
<220> FEATURE:
<223> OTHER INFORMATION: Primer for PCR multiplication

<400> SEQUENCE: 34
tcgagcgaac ctccacccgg agtcgcaaca tgatgagtcc tccaactcgg cata      54

<210> SEQ ID NO 35
<211> LENGTH: 32
<212> TYPE: PRT
<213> ORGANISM: Artificial
<220> FEATURE:
<223> OTHER INFORMATION: Ferrite-binding peptide

<400> SEQUENCE: 35

Met Pro Ser Trp Arg Thr His His Val Ala Thr Pro Gly Gly Gly Ser
1               5                   10                  15

Gly Gly Gly Ser Met Gln Thr His His Thr Thr Val Thr Ser Trp Thr
            20                  25                  30

<210> SEQ ID NO 36
<211> LENGTH: 106
<212> TYPE: DNA
<213> ORGANISM: Artificial
<220> FEATURE:
<223> OTHER INFORMATION: Primer for PCR multiplication

<400> SEQUENCE: 36
gatccatgcc gagttggagg actcatcatg ttgcgactcc gggcggcggc agcggcggcg      60
gcagcatgca gacgcatcat actacggtga cttcgtggac tgagct                    106

<210> SEQ ID NO 37
<211> LENGTH: 98
<212> TYPE: DNA
<213> ORGANISM: Artificial
<220> FEATURE:
<223> OTHER INFORMATION: Primer for PCR multiplication

<400> SEQUENCE: 37
ccggctgatg acgaatatac ggcggccacc accagttgct gccgccgccg ctgccgccgc      60
cgctcgccgg ccaccacact ttccacgcat gcggccag                             98

<210> SEQ ID NO 38
<211> LENGTH: 4
<212> TYPE: PRT
<213> ORGANISM: Artificial
<220> FEATURE:
<223> OTHER INFORMATION: linker sequence

<400> SEQUENCE: 38

```
-continued

Gly Gly Gly Ser
1

<210> SEQ ID NO 39
<211> LENGTH: 8
<212> TYPE: PRT
<213> ORGANISM: Artificial
<220> FEATURE:
<223> OTHER INFORMATION: Linker

<400> SEQUENCE: 39

Gly Gly Gly Ser Gly Gly Gly Ser
1               5
```